(12) United States Patent
Vind et al.

(10) Patent No.: US 9,879,241 B2
(45) Date of Patent: Jan. 30, 2018

(54) GLUCOAMYLASE VARIANTS AND POLYNUCLEOTIDES ENCODING SAME AND USES THEREOF

(71) Applicant: NOVOZYMES A/S, Bagsvaerd (DK)

(72) Inventors: Jesper Vind, Bagsvaerd (DK); Esben Peter Friis, Bagsvaerd (DK); Thomas Agsersten Poulsen, Bagsvaerd (DK); Michael Skjøt, Bagsvaerd (DK); Peter Kamp Hansen, Bagsvaerd (DK); Frank Winther Rasmussen, Bagsvaerd (DK); Steen Krogsgaard, Bagsvaerd (DK); Joyce Craig, Franklinton, NC (US); Guillermo Coward-Kelly, Franklinton, NC (US); Keiichi Ayabe, Chiba (JP)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/426,051

(22) PCT Filed: Sep. 6, 2013

(86) PCT No.: PCT/US2013/058427
§ 371 (c)(1),
(2) Date: Mar. 4, 2015

(87) PCT Pub. No.: WO2014/039773
PCT Pub. Date: Mar. 13, 2014

(65) Prior Publication Data
US 2015/0232824 A1  Aug. 20, 2015

Related U.S. Application Data

(60) Provisional application No. 61/698,170, filed on Sep. 7, 2012.

(51) Int. Cl.
| | | |
|---|---|---|
| *C12N 9/24* | (2006.01) | |
| *C12P 7/04* | (2006.01) | |
| *C12N 9/34* | (2006.01) | |
| *C12N 9/30* | (2006.01) | |
| *C12P 7/10* | (2006.01) | |
| *C12P 19/02* | (2006.01) | |
| *C12P 19/24* | (2006.01) | |
| *C12N 15/52* | (2006.01) | |

(52) U.S. Cl.
CPC ........... *C12N 9/2428* (2013.01); *C12N 9/242* (2013.01); *C12N 15/52* (2013.01); *C12P 7/10* (2013.01); *C12P 19/02* (2013.01); *C12P 19/24* (2013.01)

(58) Field of Classification Search
CPC .................................... C12N 9/24; C12P 7/04
See application file for complete search history.

(56) References Cited

U.S. PATENT DOCUMENTS

| | | | |
|---|---|---|---|
| 8,058,033 B2 | 11/2011 | Aehle | |
| 8,101,392 B2 | 1/2012 | Nielsen | |
| 2006/0172403 A1* | 8/2006 | Udagawa | C12N 9/242 435/161 |
| 2010/0196537 A1* | 8/2010 | Konieczny-Janda | C12P 7/06 426/53 |
| 2010/0216213 A1* | 8/2010 | Udagawa | C12N 9/242 435/203 |
| 2011/0033900 A1* | 2/2011 | Dunn-Coleman | C12N 9/2417 435/96 |
| 2012/0214196 A1* | 8/2012 | Landvik | C12N 9/2428 435/43 |
| 2012/0219989 A1* | 8/2012 | Landvik | C12N 9/2428 435/69.1 |
| 2013/0137152 A1* | 5/2013 | Landvik | C12N 9/26 435/162 |
| 2013/0280774 A1* | 10/2013 | Blake | C12N 9/88 435/146 |
| 2013/0333072 A1* | 12/2013 | Landvik | C12P 7/10 800/298 |
| 2014/0007301 A1* | 1/2014 | Morant | C12N 9/2428 800/298 |

FOREIGN PATENT DOCUMENTS

| | | |
|---|---|---|
| EP | 2009098 A1 | 12/2008 |
| WO | 99/28448 A1 | 6/1999 |
| WO | 2006/069289 A2 | 6/2006 |
| WO | 2011/066560 A1 | 6/2011 |
| WO | 2011/066576 A1 | 6/2011 |
| WO | 2014/177546 A2 | 11/2014 |

OTHER PUBLICATIONS

GenBank Accession No. EIW63814, Glucoamylase—Jun. 2012.

* cited by examiner

*Primary Examiner* — Maryam Monshipouri
(74) *Attorney, Agent, or Firm* — David Fazzolare

(57) ABSTRACT

The present invention relates to variants of a parent glucoamylase. The present invention also relates to polynucleotides encoding the variants; nucleic acid constructs, vectors, and host cells comprising the polynucleotides; and methods of using the glucoamylase variants.

16 Claims, No Drawings

SEQUENCE LISTING

<160> NUMBER OF SEQ ID NOS: 4

<210> SEQ ID NO 1
<211> LENGTH: 2166
<212> TYPE: DNA
<213> ORGANISM: Trametes cingulata
<220> FEATURE:
<221> NAME/KEY: sig_peptide
<222> LOCATION: (1)..(54)
<220> FEATURE:
<221> NAME/KEY: CDS
<222> LOCATION: (1)..(162)
<220> FEATURE:
<221> NAME/KEY: mat_peptide
<222> LOCATION: (55)..(2166)
<220> FEATURE:
<221> NAME/KEY: Intron
<222> LOCATION: (163)..(247)
<220> FEATURE:
<221> NAME/KEY: CDS
<222> LOCATION: (248)..(521)
<220> FEATURE:
<221> NAME/KEY: Intron
<222> LOCATION: (522)..(577)
<220> FEATURE:
<221> NAME/KEY: CDS
<222> LOCATION: (578)..(722)
<220> FEATURE:
<221> NAME/KEY: Intron
<222> LOCATION: (723)..(772)
<220> FEATURE:
<221> NAME/KEY: CDS
<222> LOCATION: (773)..(932)
<220> FEATURE:
<221> NAME/KEY: Intron
<222> LOCATION: (933)..(1001)
<220> FEATURE:
<221> NAME/KEY: CDS
<222> LOCATION: (1002)..(1277)
<220> FEATURE:
<221> NAME/KEY: Intron
<222> LOCATION: (1278)..(1341)
<220> FEATURE:
<221> NAME/KEY: CDS
<222> LOCATION: (1342)..(1807)
<220> FEATURE:
<221> NAME/KEY: misc_feature
<222> LOCATION: (1744)..(1773)
<223> OTHER INFORMATION: Linker region
<220> FEATURE:
<221> NAME/KEY: misc_feature
<222> LOCATION: (1774)..(2166)
<223> OTHER INFORMATION: binding domain
<220> FEATURE:
<221> NAME/KEY: Intron
<222> LOCATION: (1808)..(1864)
<220> FEATURE:
<221> NAME/KEY: CDS
<222> LOCATION: (1865)..(1963)
<220> FEATURE:
<221> NAME/KEY: Intron
<222> LOCATION: (1964)..(2023)
<220> FEATURE:
<221> NAME/KEY: CDS
<222> LOCATION: (2024)..(2163)

<400> SEQUENCE: 1 atg cgt ttc acg ctc ctc acc tcc ctc ctg ggc ctc gcc ctc ggc gcg     48
Met Arg Phe Thr Leu Leu Thr Ser Leu Leu Gly Leu Ala Leu Gly Ala
            -15                 -10                 -5 ttc gcg cag tcg agt gcg gcc gac gcg tac gtc gcg tcc gaa tcg ccc     96
Phe Ala Gln Ser Ser Ala Ala Asp Ala Tyr Val Ala Ser Glu Ser Pro
    -1   1               5                  10 atc gcc aag gcg ggt gtg ctc gcc aac atc ggg ccc agc ggc tcc aag    144
Ile Ala Lys Ala Gly Val Leu Ala Asn Ile Gly Pro Ser Gly Ser Lys

```
                15                  20                  25                  30
tcc aac gga gca aag gca agtgacacag tgacactccg gggcgcccat              192
Ser Asn Gly Ala Lys Ala
                35 gcttcattct tctgtgcaca tggtagcgct gacatatcgt tgttttt gac agccc ggc    250
                                                            Gly atc gtg att gca agt ccg agc aca tcc aac ccg aac tac ctg tac aca     298
Ile Val Ile Ala Ser Pro Ser Thr Ser Asn Pro Asn Tyr Leu Tyr Thr
                40                  45                  50 tgg acg cgc gac tcg tcc ctc gtg ttc aag gcg ctc atc gac cag ttc     346
Trp Thr Arg Asp Ser Ser Leu Val Phe Lys Ala Leu Ile Asp Gln Phe
        55                  60                  65 acc act ggc gaa gat acc tcg ctc cga act ctg att gac gag ttc acc     394
Thr Thr Gly Glu Asp Thr Ser Leu Arg Thr Leu Ile Asp Glu Phe Thr
70                  75                  80                  85 tcg gcg gag gcc ata ctc cag cag gtg ccg aac ccg agc ggg aca gtc     442
Ser Ala Glu Ala Ile Leu Gln Gln Val Pro Asn Pro Ser Gly Thr Val
                90                  95                  100 agc act gga ggc ctc ggc gag ccc aag ttc aac atc gac gag acc gcg    490
Ser Thr Gly Gly Leu Gly Glu Pro Lys Phe Asn Ile Asp Glu Thr Ala
                105                 110                 115 ttc acg gat gcc tgg ggt cgt cct cag cgc g gtaagtcgga ggttgcctcg     541
Phe Thr Asp Ala Trp Gly Arg Pro Gln Arg
                120                 125 acggagatac gcccagactg acttcaagac tctcag at ggt ccc gct ctc cgg      594
                                           Asp Gly Pro Ala Leu Arg
                                                       130 gcg act gcc atc atc acc tac gcc aac tgg ctc ctc gac aac aag aac    642
Ala Thr Ala Ile Ile Thr Tyr Ala Asn Trp Leu Leu Asp Asn Lys Asn
    135                 140                 145 acg acc tac gtg acc aac act ctc tgg cct atc atc aag ctc gac ctc    690
Thr Thr Tyr Val Thr Asn Thr Leu Trp Pro Ile Ile Lys Leu Asp Leu
150                 155                 160                 165 gac tac gtc gcc agc aac tgg aac cag tcc ac  gtatgttctc taaattctct  742
Asp Tyr Val Ala Ser Asn Trp Asn Gln Ser Thr
                170                 175 cccgtgggta accagtctga acgttcatag g ttt gat ctc tgg gag gag att     794
                                  Phe Asp Leu Trp Glu Glu Ile
                                                      180 aac tcc tcg tcg ttc ttc act acc gcc gtc cag cac cgt gct ctg cgc    842
Asn Ser Ser Ser Phe Phe Thr Thr Ala Val Gln His Arg Ala Leu Arg
                185                 190                 195 gag ggc gcg act ttc gct aat cgc atc gga caa acc tcg gtg gtc agc    890
Glu Gly Ala Thr Phe Ala Asn Arg Ile Gly Gln Thr Ser Val Val Ser
200                 205                 210                 215 ggg tac acc acc caa gca aac aac ctt ctc tgc ttc ctg cag           932
Gly Tyr Thr Thr Gln Ala Asn Asn Leu Leu Cys Phe Leu Gln
                220                 225 gcagtctatc ccgtcacacg tctgtctgtt ccgttttcc cacagctcac ctcgtcccgg   992 gccctgtag tcg tac tgg aac ccc acc ggc ggc tat atc acc gca aac acg 1043
            Ser Tyr Trp Asn Pro Thr Gly Gly Tyr Ile Thr Ala Asn Thr
                230                 235                 240 ggc ggc ggc cgc tct ggc aag gac gcg aac acc gtt ctc acg tcg atc    1091
Gly Gly Gly Arg Ser Gly Lys Asp Ala Asn Thr Val Leu Thr Ser Ile
                245                 250                 255 cac acc ttc gac ccg gcc gct gga tgc gac gct gtt acg ttc cag ccg    1139
His Thr Phe Asp Pro Ala Ala Gly Cys Asp Ala Val Thr Phe Gln Pro
260                 265                 270                 275
```

```
tgc tcg gac aag gcg ctg tcg aac ttg aag gtg tac gtc gat gcg ttc      1187
Cys Ser Asp Lys Ala Leu Ser Asn Leu Lys Val Tyr Val Asp Ala Phe
            280                 285                 290 cgc tcg atc tac tcc atc aac agc ggg atc gcc tcg aat gcg gcc gtt      1235
Arg Ser Ile Tyr Ser Ile Asn Ser Gly Ile Ala Ser Asn Ala Ala Val
            295                 300                 305 gct acc ggc cgc tac ccc gag gac agc tac atg ggc gga aac              1277
Ala Thr Gly Arg Tyr Pro Glu Asp Ser Tyr Met Gly Gly Asn
            310                 315                 320 gtgagcgacc atttctgtgc gtacaccgcg gtcgcgttaa ctgagatgtt ctcctctcct    1337 gtag cca tgg tac ctc acc acc tcc gcc gtc gct gag cag ctc tac gat    1386
     Pro Trp Tyr Leu Thr Thr Ser Ala Val Ala Glu Gln Leu Tyr Asp
                 325                 330                 335 gcg ctc att gtg tgg aac aag ctt ggc gcc ctg aac gtc acg agc acc      1434
Ala Leu Ile Val Trp Asn Lys Leu Gly Ala Leu Asn Val Thr Ser Thr
            340                 345                 350 tcc ctc ccc ttc ttc cag cag ttc tcg tca ggc gtc acc gtc ggc acc      1482
Ser Leu Pro Phe Phe Gln Gln Phe Ser Ser Gly Val Thr Val Gly Thr
            355                 360                 365 tat gcc tca tcc tcg tcc acc ttc aag acg ctc act tcc gcc atc aag      1530
Tyr Ala Ser Ser Ser Ser Thr Phe Lys Thr Leu Thr Ser Ala Ile Lys
            370                 375                 380 acc ttc gcc gac ggc ttc ctc gcg gtc aac gcc aag tac acg ccc tcg      1578
Thr Phe Ala Asp Gly Phe Leu Ala Val Asn Ala Lys Tyr Thr Pro Ser
385                 390                 395                 400 aac ggc ggc ctt gct gaa cag tac agc cgg agc aac ggc tcg ccc gtc      1626
Asn Gly Gly Leu Ala Glu Gln Tyr Ser Arg Ser Asn Gly Ser Pro Val
                405                 410                 415 agc gct gtg gac ctg acg tgg agc tat gct gct gcc ctc acg tcg ttt      1674
Ser Ala Val Asp Leu Thr Trp Ser Tyr Ala Ala Ala Leu Thr Ser Phe
            420                 425                 430 gct gcg cgc tca ggc aag acg tat gcg agc tgg ggc gcg gcg ggt ttg      1722
Ala Ala Arg Ser Gly Lys Thr Tyr Ala Ser Trp Gly Ala Ala Gly Leu
            435                 440                 445 act gtc ccg acg act tgc tcg ggg agt ggc ggt gct ggg act gtg gcc      1770
Thr Val Pro Thr Thr Cys Ser Gly Ser Gly Gly Ala Gly Thr Val Ala
450                 455                 460 gtc acc ttc aac gtg cag gcg acc acc gtg ttc ggc g gtgagtacgc         1817
Val Thr Phe Asn Val Gln Ala Thr Thr Val Phe Gly
465                 470                 475 catcgtatgc tactagggca gttactcata gcttgtcgga cttgtag ag aac att       1872
                                                      Glu Asn Ile tac atc aca ggc tcg gtc ccc gct ctc cag aac tgg tcg ccc gac aac      1920
Tyr Ile Thr Gly Ser Val Pro Ala Leu Gln Asn Trp Ser Pro Asp Asn
480                 485                 490                 495 gcg ctc atc ctc tca gcg gcc aac tac ccc act tgg agc agt a            1963
Ala Leu Ile Leu Ser Ala Ala Asn Tyr Pro Thr Trp Ser Ser
                500                 505 cgtctgaacc gccttcagcc tgcttcatac gttcgctgac atcgggcatc catctagtca    2023 cc gtg aac ctg ccg gcg agc acg acg atc gag tac aag tac att cgc       2070
   Thr Val Asn Leu Pro Ala Ser Thr Thr Ile Glu Tyr Lys Tyr Ile Arg
510                 515                 520                 525 aag ttc aac ggc gcg gtc acc tgg gag tcc gac ccg aac aac tcg atc      2118
Lys Phe Asn Gly Ala Val Thr Trp Glu Ser Asp Pro Asn Asn Ser Ile
                530                 535                 540 acg acg ccc gcg agc ggc acg ttc acc cag aac gac acc tgg cgg tag      2166
Thr Thr Pro Ala Ser Gly Thr Phe Thr Gln Asn Asp Thr Trp Arg
            545                 550                 555
```

<210> SEQ ID NO 2
<211> LENGTH: 574
<212> TYPE: PRT
<213> ORGANISM: Trametes cingulata

<400> SEQUENCE: 2

```
Met Arg Phe Thr Leu Leu Thr Ser Leu Leu Gly Leu Ala Leu Gly Ala
            -15                 -10                  -5

Phe Ala Gln Ser Ser Ala Ala Asp Ala Tyr Val Ala Ser Glu Ser Pro
     -1  1               5                  10

Ile Ala Lys Ala Gly Val Leu Ala Asn Ile Gly Pro Ser Gly Ser Lys
 15                  20                  25                  30

Ser Asn Gly Ala Lys Ala Gly Ile Val Ile Ala Ser Pro Ser Thr Ser
                 35                  40                  45

Asn Pro Asn Tyr Leu Tyr Thr Trp Thr Arg Asp Ser Ser Leu Val Phe
             50                  55                  60

Lys Ala Leu Ile Asp Gln Phe Thr Thr Gly Glu Asp Thr Ser Leu Arg
             65                  70                  75

Thr Leu Ile Asp Glu Phe Thr Ser Ala Glu Ala Ile Leu Gln Gln Val
 80                  85                  90

Pro Asn Pro Ser Gly Thr Val Ser Thr Gly Gly Leu Gly Glu Pro Lys
 95                 100                 105                 110

Phe Asn Ile Asp Glu Thr Ala Phe Thr Asp Ala Trp Gly Arg Pro Gln
                115                 120                 125

Arg Asp Gly Pro Ala Leu Arg Ala Thr Ala Ile Ile Thr Tyr Ala Asn
            130                 135                 140

Trp Leu Leu Asp Asn Lys Asn Thr Thr Tyr Val Thr Asn Thr Leu Trp
            145                 150                 155

Pro Ile Ile Lys Leu Asp Leu Asp Tyr Val Ala Ser Asn Trp Asn Gln
            160                 165                 170

Ser Thr Phe Asp Leu Trp Glu Glu Ile Asn Ser Ser Phe Phe Thr
175                 180                 185                 190

Thr Ala Val Gln His Arg Ala Leu Arg Glu Gly Ala Thr Phe Ala Asn
                195                 200                 205

Arg Ile Gly Gln Thr Ser Val Val Ser Gly Tyr Thr Thr Gln Ala Asn
            210                 215                 220

Asn Leu Leu Cys Phe Leu Gln Ser Tyr Trp Asn Pro Thr Gly Gly Tyr
            225                 230                 235

Ile Thr Ala Asn Thr Gly Gly Gly Arg Ser Gly Lys Asp Ala Asn Thr
240                 245                 250

Val Leu Thr Ser Ile His Thr Phe Asp Pro Ala Ala Gly Cys Asp Ala
255                 260                 265                 270

Val Thr Phe Gln Pro Cys Ser Asp Lys Ala Leu Ser Asn Leu Lys Val
                275                 280                 285

Tyr Val Asp Ala Phe Arg Ser Ile Tyr Ser Ile Asn Ser Gly Ile Ala
            290                 295                 300

Ser Asn Ala Ala Val Ala Thr Gly Arg Tyr Pro Glu Asp Ser Tyr Met
            305                 310                 315

Gly Gly Asn Pro Trp Tyr Leu Thr Thr Ser Ala Val Ala Glu Gln Leu
            320                 325                 330

Tyr Asp Ala Leu Ile Val Trp Asn Lys Leu Gly Ala Leu Asn Val Thr
335                 340                 345                 350

Ser Thr Ser Leu Pro Phe Phe Gln Gln Phe Ser Ser Gly Val Thr Val
                355                 360                 365
```

```
Gly Thr Tyr Ala Ser Ser Ser Thr Phe Lys Thr Leu Thr Ser Ala
                370                 375                 380

Ile Lys Thr Phe Ala Asp Gly Phe Leu Ala Val Asn Ala Lys Tyr Thr
            385                 390                 395

Pro Ser Asn Gly Gly Leu Ala Glu Gln Tyr Ser Arg Ser Asn Gly Ser
400                 405                 410

Pro Val Ser Ala Val Asp Leu Thr Trp Ser Tyr Ala Ala Ala Leu Thr
415                 420                 425                 430

Ser Phe Ala Ala Arg Ser Gly Lys Thr Tyr Ala Ser Trp Gly Ala Ala
                435                 440                 445

Gly Leu Thr Val Pro Thr Thr Cys Ser Gly Ser Gly Ala Gly Thr
                450                 455                 460

Val Ala Val Thr Phe Asn Val Gln Ala Thr Thr Val Phe Gly Glu Asn
                465                 470                 475

Ile Tyr Ile Thr Gly Ser Val Pro Ala Leu Gln Asn Trp Ser Pro Asp
            480                 485                 490

Asn Ala Leu Ile Leu Ser Ala Ala Asn Tyr Pro Thr Trp Ser Ser Thr
495                 500                 505                 510

Val Asn Leu Pro Ala Ser Thr Thr Ile Glu Tyr Lys Tyr Ile Arg Lys
                515                 520                 525

Phe Asn Gly Ala Val Thr Trp Glu Ser Asp Pro Asn Asn Ser Ile Thr
                530                 535                 540

Thr Pro Ala Ser Gly Thr Phe Thr Gln Asn Asp Thr Trp Arg
                545                 550                 555
```

<210> SEQ ID NO 3
<211> LENGTH: 1725
<212> TYPE: DNA
<213> ORGANISM: Trametes cingulata
<220> FEATURE:
<221> NAME/KEY: misc_feature
<222> LOCATION: (1)..(1725)
<223> OTHER INFORMATION: cDNA
<220> FEATURE:
<221> NAME/KEY: misc_feature
<222> LOCATION: (55)..(1725)
<223> OTHER INFORMATION: coding region of cDNA
<220> FEATURE:
<221> NAME/KEY: misc_feature
<222> LOCATION: (1420)..(1725)
<223> OTHER INFORMATION: binding domain

<400> SEQUENCE: 3

```
atgcgtttca cgctcctcac ctccctcctg ggcctcgccc tcggcgcgtt cgcgcagtcg      60
agtgcggccg acgcgtacgt cgcgtccgaa tcgcccatcg ccaaggcggg tgtgctcgcc     120
aacatcgggc ccagcggctc caagtccaac ggagcaaagg caggcatcgt gattgcaagt     180
ccgagcacat ccaacccgaa ctacctgtac acatggacgc gcgactcgtc cctcgtgttc     240
aaggcgctca tcgaccagtt caccactggc gaagatacct cgctccgaac tctgattgac     300
gagttcacct cggcggaggc catactccag caggtgccga acccgagcgg acagtcagc     360 actggaggcc tcggcgagcc caagttcaac atcgacgaga ccgcgttcac ggatgcctgg     420
ggtcgtcctc agcgcgatgg tcccgctctc cgggcgactg ccatcatcac ctacgccaac     480
tggctcctcg acaacaagaa cacgacctac gtgaccaaca ctctctggcc tatcatcaag     540
ctcgacctcg actacgtcgc cagcaactgg aaccagtcca cgtttgatct ctgggaggag     600
attaactcct cgtcgttctt cactaccgcc gtccagcacc gtgctctgcg cgagggcgcg     660
```

-continued

```
actttcgcta atcgcatcgg acaaacctcg gtggtcagcg ggtacaccac ccaagcaaac     720
aaccttctct gcttcctgca gtcgtactgg aaccccaccg gcggctatat caccgcaaac     780
acgggcggcg gccgctctgg caaggacgcg aacaccgttc tcacgtcgat ccacaccttc     840
gacccggccg ctggatgcga cgctgttacg ttccagccgt gctcggacaa ggcgctgtcg     900
aacttgaagg tgtacgtcga tgcgttccgc tcgatctact ccatcaacag cgggatcgcc     960
tcgaatgcgg ccgttgctac cggccgctac cccgaggaca gctacatggg cggaaaccca    1020
tggtacctca ccacctccgc cgtcgctgag cagctctacg atgcgctcat tgtgtggaac    1080
aagcttggcg ccctgaacgt cacgagcacc tccctccccct tcttccagca gttctcgtca    1140
ggcgtcaccg tcggcaccta tgcctcatcc tcgtccacct tcaagacgct cacttccgcc    1200
atcaagacct tcgccgacgg cttcctcgcg gtcaacgcca agtacacgcc ctcgaacggc    1260
ggccttgctg aacagtacag ccggagcaac ggctcgcccg tcagcgctgt ggacctgacg    1320
tggagctatg ctgctgccct cacgtcgttt gctgcgcgct caggcaagac gtatgcgagc    1380
tggggcgcgg cgggtttgac tgtcccgacg acttgctcgg ggagtggcgg tgctgggact    1440
gtggccgtca ccttcaacgt gcaggcgacc accgtgttcg gcgagaacat ttacatcaca    1500
ggctcggtcc ccgctctcca gaactggtcg cccgacaacg cgctcatcct ctcagcggcc    1560
aactacccca cttggagcag taccgtgaac ctgccggcga gcacgacgat cgagtacaag    1620
tacattcgca agttcaacgg cgcggtcacc tgggagtccg acccgaacaa ctcgatcacg    1680
acgcccgcga gcggcacgtt cacccagaac gacacctggc ggtag                    1725
```

<210> SEQ ID NO 4
<211> LENGTH: 583
<212> TYPE: PRT
<213> ORGANISM: Rhizomucor pusillus

<400> SEQUENCE: 4

```
Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190
```

```
His Ile Arg Lys Asp Phe Trp Thr Gly Tyr Ala Glu Ala Ala Gly Val
            195                 200                 205
Phe Ala Thr Gly Glu Val Phe Asn Gly Asp Pro Ala Tyr Val Gly Pro
210                 215                 220
Tyr Gln Lys Tyr Leu Pro Ser Leu Ile Asn Tyr Pro Met Tyr Tyr Ala
225                 230                 235                 240
Leu Asn Asp Val Phe Val Ser Lys Ser Lys Gly Phe Ser Arg Ile Ser
            245                 250                 255
Glu Met Leu Gly Ser Asn Arg Asn Ala Phe Glu Asp Thr Ser Val Leu
                260                 265                 270
Thr Thr Phe Val Asp Asn His Asp Asn Pro Arg Phe Leu Asn Ser Gln
            275                 280                 285
Ser Asp Lys Ala Leu Phe Lys Asn Ala Leu Thr Tyr Val Leu Leu Gly
290                 295                 300
Glu Gly Ile Pro Ile Val Tyr Tyr Gly Ser Glu Gln Gly Phe Ser Gly
305                 310                 315                 320
Gly Ala Asp Pro Ala Asn Arg Glu Val Leu Trp Thr Thr Asn Tyr Asp
            325                 330                 335
Thr Ser Ser Asp Leu Tyr Gln Phe Ile Lys Thr Val Asn Ser Val Arg
                340                 345                 350
Met Lys Ser Asn Lys Ala Val Tyr Met Asp Ile Tyr Val Gly Asp Asn
            355                 360                 365
Ala Tyr Ala Phe Lys His Gly Asp Ala Leu Val Val Leu Asn Asn Tyr
370                 375                 380
Gly Ser Gly Ser Thr Asn Gln Val Ser Phe Ser Val Ser Gly Lys Phe
385                 390                 395                 400
Asp Ser Gly Ala Ser Leu Met Asp Ile Val Ser Asn Ile Thr Thr Thr
            405                 410                 415
Val Ser Ser Asp Gly Thr Val Thr Phe Asn Leu Lys Asp Gly Leu Pro
                420                 425                 430
Ala Ile Phe Thr Ser Ala Thr Gly Gly Thr Thr Thr Ala Thr Pro
            435                 440                 445
Thr Gly Ser Gly Ser Val Thr Ser Thr Ser Lys Thr Thr Ala Thr Ala
450                 455                 460
Ser Lys Thr Ser Thr Ser Thr Ser Ser Thr Ser Cys Thr Thr Pro Thr
465                 470                 475                 480
Ala Val Ala Val Thr Phe Asp Leu Thr Ala Thr Thr Thr Tyr Gly Glu
            485                 490                 495
Asn Ile Tyr Leu Val Gly Ser Ile Ser Gln Leu Gly Asp Trp Glu Thr
                500                 505                 510
Ser Asp Gly Ile Ala Leu Ser Ala Asp Lys Tyr Thr Ser Ser Asp Pro
            515                 520                 525
Leu Trp Tyr Val Thr Val Thr Leu Pro Ala Gly Glu Ser Phe Glu Tyr
530                 535                 540
Lys Phe Ile Arg Ile Glu Ser Asp Asp Ser Val Glu Trp Glu Ser Asp
545                 550                 555                 560
Pro Asn Arg Glu Tyr Thr Val Pro Gln Ala Cys Gly Thr Ser Thr Ala
            565                 570                 575
Thr Val Thr Asp Thr Trp Arg
                580
```

US 9,879,241 B2

GLUCOAMYLASE VARIANTS AND POLYNUCLEOTIDES ENCODING SAME AND USES THEREOF

CROSS-REFERENCE TO RELATED APPLICATIONS

This application is a 35 U.S.C. 371 national application of PCT/US2013/058427 filed Sep. 6, 2013, which claims priority or the benefit under 35 U.S.C. 119 of U.S. provisional application No. 61/698,170 filed Sep. 7, 2012, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to variants of a parent glucoamylase, polynucleotides encoding the variants, methods of producing the variants, and methods/processes of using the variants for, e.g., starch conversion to producing products such as syrups, such as glucose or High Fructose Corn Syrup (HFCS); or fermentation products, such as ethanol. The invention also relates to a composition comprising a glucoamylase variant of the invention.

BACKGROUND OF THE INVENTION

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules.

Commercially, glucoamylases are used to convert starchy material, which may already be partially hydrolyzed, e.g., by an alpha-amylase, to glucose. The glucose may then be converted directly or indirectly into a fermentation product, such as ethanol, using a fermenting organism. The end product may also be syrup. For instance, the end product may be glucose, but may also be converted, e.g., by glucose isomerase to fructose or a mixture of glucose and fructose. Glucoamylases are produced by several filamentous fungi and yeast including *Aspergillus niger*.

WO 99/28448 concerns a glucoamylase derived from *Talaromyces emersonii* and the use thereof for producing fermentation products.

WO 2006/069289 discloses a glucoamylase derived from *Trametes cingulata*, *Pachykytospora papyracea* and *Leucopaxillus giganteus* and the use thereof in processes for manufacturing fermentation products.

The present invention provides variants of parent glucoamylases with improved properties compared to its parent. More specifically it is an object of the present invention to provide glucoamylase variants which provide a higher saccharification yield and yield in fermentation product production processes, such as ethanol production processes, including conventional ethanol production processes based on gelatinized starch-containing material and/or raw starch hydrolysis (RSH) processes (i.e., one-step ethanol fermentation processes) based on un-gelatinized (or uncooked) starch.

SUMMARY OF THE INVENTION

The present invention provides variants of a parent glucoamylase that is more efficient in, e.g., fermentation product production processes, especially ethanol production processes, including conventional ethanol production processes based on gelatinized starch-containing material and/or raw starch hydrolysis (RSH) processes (i.e., one-step ethanol fermentation processes) based on un-gelatinized (or uncooked) starch.

In the first aspect the present invention relates to variants of parent glucoamylase, comprising an alteration at one or more (several) positions corresponding to positions: 20; 90; 121; 369; 397; 405, 408; 466; 470; 474; 539; and 552; of the mature polypeptide of SEQ ID NO: 2 wherein each alteration is independently a substitution; and the variant has glucoamylase activity.

In an embodiment a variant comprises one or more (several) of the following substitutions in SEQ ID NOS: 2 or in one or more corresponding positions selected from the group consisting of: V20L; I90G; A121S, Y369F; Y397T; A405R, Y408F; T466S, Q470T; V474K; N539T; and N552T or Y. Such variants have increased ethanol yields in a conventional ethanol process and/or in a raw starch hydrolysis ethanol process compared to the parent glucoamylase.

The present invention also relates to polynucleotides encoding the variants; nucleic acid constructs, vectors, and host cells comprising the polynucleotides; and methods of producing the variants.

The present invention also relates to method of using said variants for starch conversion, production of syrup and/or a fermentation product, from, e.g., gelatinized and/or un-gelatinized starch-containing material; in a process for producing oligosaccharides; in a process for producing specialty syrups; in a process for producing ethanol, such as fuel ethanol or potable ethanol; in a fermentation process for producing organic compounds, such as citric acid, ascorbic acid, lysine, glutamic acid; in a process in a brewing process for producing a beverage, such as beer.

Definitions

Glucoamylase activity: The term "glucoamylase activity" means 1,4-alpha-D-glucan glucohydrolase activity, (EC 3.2.1.3) that catalyzes the release of D-glucose from the non-reducing ends of starch or related oligo- and polysaccharide molecules. For purposes of the present invention, glucoamylase activity is determined according to the procedure described in the "Materials and Methods"-section below. The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

In one aspect, the variants of the present invention have at least 20%, e.g., at least 40%, at least 50%, at least 60%, at least 70%, at least 80%, at least 90%, at least 95%, or at least 100% of the glucoamylase activity of the mature parent polypeptide, e.g., of SEQ ID NO: 2.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has glucoamylase activity. In one aspect, a fragment contains at least 455 amino acid residues (e.g., amino acids 1 to 455 of SEQ ID NO: 2), i.e., catalytic domain; or at least 440 amino acid residues, e.g., at least 420 and at least 400 amino acid residues.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to increased fermentation yield compared to the corresponding parent glucoamylase in, e.g., a raw starch hydrolysis process for producing ethanol and/or a conventional ethanol production process.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 556 of SEQ ID NO: 2. The SignalP (Nielsen et al., 1997, *Protein Engineering* 10: 1-6). program predicts amino acids −1 to −18 of SEQ ID NO: 2 to be the signal peptide.

Mature polypeptide coding sequence: The term "mature polypeptide coding sequence" means a polynucleotide that encodes a mature polypeptide having glucoamylase activity. In one aspect, the mature polypeptide coding sequence is nucleotides 55 to 1722 of SEQ ID NO: 3 based on the SignalP program (Nielsen et al., 1997, *Protein Engineering* 10: 1-6) that predicts nucleotides 1 to 54 of SEQ ID NO: 3 to encode a signal peptide. In one aspect, the mature polypeptide coding sequence is nucleotides 55 to 1722 of SEQ ID NO: 3 based on the SignalP program (Nielsen et al., 1997, *Protein Engineering* 10: 1-6).

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent Glucoamylase: The term "parent" or "parent glucoamylase" means a glucoamylase to which an alteration is made to produce the variants of the present invention. The parent may be a naturally occurring (wild-type) polypeptide or a variant or fragment thereof. In a preferred embodiment the parent glucoamylase is the one shown in SEQ ID NO: 2.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment).

Subsequence: The term "subsequence" means a polynucleotide having one or more (e.g., several) nucleotides absent from the 5' and/or 3' end of a mature polypeptide coding sequence; wherein the subsequence encodes a fragment having glucoamylase activity. In one aspect, a subsequence contains at least 1365 nucleotides (e.g., nucleotides 55 to 1419 of SEQ ID NO: 3.

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the glucoamylase activity of the mature parent polypeptide, e.g., of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type Glucoamylase: The term "wild-type" glucoamylase means a glucoamylase expressed by a naturally occurring microorganism, such as a bacterium, yeast, or filamentous fungus found in nature.

Conventions for Designation of Variants

For purposes of the present invention, the mature polypeptide disclosed in SEQ ID NO: 2 is used to determine the corresponding amino acid residue in another glucoamylase. The amino acid sequence of another gluocoamylase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another glucoamylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The inventors have surprisingly found that certain glucoamylase variants, as defined herein, work more efficiently in corn-to-ethanol processes than a corresponding parent glucoamylase enzyme. As shown in the Examples variants of the parent glucoamylase shown in SEQ ID NO: 2 were tested in a conventional ethanol production process and in a raw starch hydrolysis process. A number of the glucoamylase variants that was tested in combination with an alpha-amylase provided a relatively higher performance relative to the parent glucoamylase under the same conditions.

Variants

The present invention relates to variants of a parent glucoamylase, comprising an alteration at one or more (several) positions corresponding to positions: 20; 90; 121; 369; 397; 405; 408; 466; 470; 474; 539; and 552;
of the mature polypeptide of SEQ ID NO: 2 wherein each alteration is independently a substitution and the variant has glucoamylase activity.

In a preferred embodiment, the alteration is a substitution.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent glucoamylase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100% sequence identity to the mature polypeptide of SEQ ID NO: 2.

In one aspect, the number of alterations in the variants of the present invention is 1-20, e.g., 1-10 and 1-5, such as 1, 2, 3, 4, 5, 6, 7, 8, 9 or 10 alterations.

In an embodiment the variant comprises one or more (several) of the following substitutions in SEQ ID NO: 2 or in one or more corresponding positions selected from the group consisting of: V20L, I90G, A121S, Y369F, Y397T, A405R, Y408F, T466S, Q470T, V474K, N539T, and N552T or Y.

In another aspect, a variant comprises an alteration at two positions corresponding to any of positions V20L, I90G, A121S, Y369F, Y397T A405R, Y408F, T466S, Q470T, V474K, N539T, and N552T or Y.

In another aspect, a variant comprises an alteration at three positions corresponding to any of positions V20L, I90G, A121S, Y369F, Y397T, A405R, Y408F, T466S, Q470T, V474K, N539T, and N552T or Y.

In another aspect, a variant comprises an alteration at four positions corresponding to any of positions V20L, I90G, A121S, Y369F, Y397T, A405R, Y408F, T466S, Q470T, V474K, N539T, and N552T or Y.

In another aspect, a variant comprises an alteration at five positions corresponding to any of positions V20L, I90G, A121S, Y369F, Y397T, A405R, Y408F, T466S, Q470T, V474K, N539T, and N552T or Y.

In another aspect, a variant comprises an alteration at six positions corresponding to any of positions V20L, I90G, A121S, Y369F, Y397T, A405R, Y408F, T466S, Q470T, V474K, N539T, and N552T or Y.

In another aspect, a variant comprises an alteration at seven positions corresponding to any of positions V20L, I90G, A121S, Y369F, Y397T, A405R, Y408F, T466S, Q470T, V474K, N539T, and N552T or Y.

In another aspect, a variant comprises an alteration at eight positions corresponding to any of positions V20L, I90G, A121S, Y369F, Y397T, A405R, Y408F, T466S, Q470T, V474K, N539T, and N552T or Y.

In another aspect, a variant comprises an alteration at nine positions corresponding to any of positions V20L, I90G, A121S, Y369F, Y397T, A405R, Y408F, T466S, Q470T, V474K, N539T, and N552T or Y.

In another aspect, a variant comprises an alteration at ten positions corresponding to any of positions V20L, I90G, A121S, Y369F, Y397T, A405R, Y408F, T466S, Q470T, V474K, N539T, and N552T or Y.

In another aspect, a variant comprises an alteration at eleven positions corresponding to any of positions V20L, I90G, A121S, Y369F, Y397T, A405R, Y408F, T466S, Q470T, V474K, N539T, and N552T or Y.

In a preferred embodiment the variant has one or more (several) of the following substitutions: V20L; Y369F and N552T or N552Y.

In another aspect, a variant comprises an alteration at two positions corresponding to any of positions V20L; Y369F and N552T or N552Y.

In another aspect, a variant comprises an alteration at three positions corresponding to any of positions V20L; Y369F and N552T or N552Y.

In another aspect, a variant comprises an alteration at all positions corresponding to positions V20L; Y369F and N552T or N552Y.

In another aspect, the variant comprises or consists of a substitution at a position corresponding to position 20. In another aspect, the amino acid at a position corresponding to position 20 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu.

In another aspect, the variant comprises or consists of a substitution at a position corresponding to position 90. In another aspect, the amino acid at a position corresponding to position 90 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly.

In another aspect, the variant comprises or consists of a substitution at a position corresponding to position 121. In another aspect, the amino acid at a position corresponding to position 121 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser.

In another aspect, the variant comprises or consists of a substitution at a position corresponding to position 369. In another aspect, the amino acid at a position corresponding to position 369 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe.

In another aspect, the variant comprises or consists of a substitution at a position corresponding to position 397. In another aspect, the amino acid at a position corresponding to position 397 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr.

In another aspect, the variant comprises or consists of a substitution at a position corresponding to position 405. In another aspect, the amino acid at a position corresponding to position 405 is substituted with Arg, Asn, Asp, Cys, Gln, Glu, Gly, His, Ile, Leu, Lys, Met, Phe, Pro, Ser, Thr, Trp, Tyr, or Val, preferably with Arg.

In another aspect, the variant comprises or consists of a substitution at a position corresponding to position 408. In another aspect, the amino acid at a position corresponding to position 408 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe.

In another aspect, the variant comprises or consists of a substitution at a position corresponding to position 466. In another aspect, the amino acid at a position corresponding to position 466 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser.

In another aspect, the variant comprises or consists of a substitution at a position corresponding to position 470. In another aspect, the amino acid at a position corresponding to position 470 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr.

In another aspect, the variant comprises or consists of a substitution at a position corresponding to position 474. In another aspect, the amino acid at a position corresponding to position 474 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys.

In another aspect, the variant comprises or consists of a substitution at a position corresponding to position 539. In another aspect, the amino acid at a position corresponding to position 539 is substituted with Ala, Arg, Asp, Cys, Gln, Glu, Gly, His, Ile, Leu, Lys, Met, Phe, Pro, Ser, Thr, Trp, Tyr, or Val, preferably with Thr.

In another aspect, the variant comprises or consists of a substitution at a position corresponding to position 552. In another aspect, the amino acid at a position corresponding to position 552 is substituted with Ala, Arg, Asp, Cys, Gln, Glu, Gly, His, Ile, Leu, Lys, Met, Phe, Pro, Ser, Thr, Trp, Tyr, or Val, preferably with Thr or Tyr.

In another aspect, the variant comprises or consists of alterations at positions corresponding to positions 20, 90, 369, 466 and 552, such as those described above. In preferred embodiments the variant is selected from the group of: V20L+Y369F; V20L+Y369F+Q470T+V474; V20L+Y369F+N552T; V20L+Y369F+Y408F; I90G+Y369F; Y369F+N539T; Y397T+N539T; Y397T+N552T; T466S+N552Y, V20L+I90G, A121S+Y408F; Y397T+Y408F+N552T and A405R+T466S.

In a preferred embodiment the variant comprises the following substitutions: V20L+Y369F;

In a preferred embodiment the variant comprises the following substitutions: V20L+Y369F+Q470T+V474.

In a preferred embodiment the variant comprises the following substitutions: V20L+Y369F+N552T.

In a preferred embodiment the variant comprises the following substitutions: V20L+Y369F+Y408F.

In a preferred embodiment the variant comprises the following substitutions: I90G+Y369F.

In a preferred embodiment the variant comprises the following substitutions: Y369F+N539T.

In a preferred embodiment the variant comprises the following substitutions: Y397T+N539T.

In a preferred embodiment the variant comprises the following substitutions: Y397T+N552T.

In a preferred embodiment the variant comprises the following substitutions: T466S+N552Y.

In a preferred embodiment the variant comprises the following substitutions: V20L+I90G, A121S+Y408F; Y397T+Y408F+N552T and A405R+T466S.

In a preferred embodiment the variant comprises the following substitutions: V20L+I90G.

In a preferred embodiment the variant comprises the following substitutions: A121S+Y408F.

In a preferred embodiment the variant comprises the following substitutions: Y397T+Y408F+N552T.

In a preferred embodiment the variant comprises the following substitutions: A405R+T466S.

Such variants have increased ethanol yields in a conventional ethanol process and/or in a raw starch hydrolysis ethanol process compared to the parent glucoamylase as disclosed in Example 1 below.

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants may consist of from 455 to 556, such as 463 to 556, 500 to 545, 510 to 535, 520 to 525 amino acids.

In an embodiment, the variant has improved pul/mal ratio compared to the parent enzyme. The I90G+Y369F glucoamylase variant is an example of such.

Parent Glucoamylases

The parent glucoamylase may be a. a polypeptide having at least 60% sequence identity to the mature polypeptide of SEQ ID NO: 2;

b. a polypeptide encoded by a polynucleotide that hybridizes under low stringency conditions with (i) the mature polypeptide coding sequence of SEQ ID NO: 3, (ii) the genomic DNA sequence comprising the mature polypeptide coding sequence of SEQ ID NO: 3, or (iii) the full-length complementary strand of (i) or (ii);

c. a polypeptide encoded by a polynucleotide having at least 60% identity to the mature polypeptide coding sequence of SEQ ID NO: 3; or d. a fragment of the mature polypeptide of SEQ ID NO: 2, which has glucoamylase activity.

In an aspect, the parent has a sequence identity to the mature polypeptide of SEQ ID NO: 2 of at least 60%, e.g., at least 65%, at least 70%, at least 75%, at least 80%, at least 85%, at least 90%, at least 95%, at least 96%, at least 97%, at least 98%, at least 99%, or 100%, and has glucoamylase activity. In one aspect, the amino acid sequence of the parent differs by no more than 1-20, e.g., 1-10 and 1-5, such as 1, 2, 3, 4, 5, 6, 7, 8, 9 or 10 substitutions compared to SEQ ID NO: 2.

In another aspect the parent comprises or consists of the amino acid sequence of SEQ ID NO: 2. In another aspect, the parent comprises or consists of the mature polypeptide of SEQ ID NO: 2. In another aspect, the parent comprises or consists of amino acids 1 to 556 of SEQ ID NO: 2. In an embodiment the parent is a fragment of the mature contains at least 455 amino acid residues (e.g., amino acids 1 to 455 of SEQ ID NO: 2), i.e., catalytic domain; or at least 440 amino acid residues, e.g., at least 420 and at least 400 amino acid residues.

In another embodiment, the parent is an allelic variant of the mature polypeptide of SEQ ID NO: 2.

SEQ ID NO: 1 discloses a gemomic DNA sequence. SEQ ID NO: 2 discloses the mature wild-type glucoamylase sequence from amino acid 1-556. SEQ ID NO: 3 discloses the cDNA sequence with a mature glucoamylase coding region from nucleotides 55-1722.

In a second aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 3, (ii) the cDNA sequence contained in the mature polypeptide coding sequence of SEQ ID NO: 3, or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, New York).

The polynucleotide of SEQ ID NO: 3 or a subsequence thereof, as well as the amino acid sequence of SEQ ID NO:

2 or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 3 or a subsequence thereof, the carrier material is used in a Southern blot.

For purposes of the present invention, hybridization indicates that the polynucleotide hybridizes to a labeled nucleotide probe corresponding to the polynucleotide shown in SEQ ID NO: 3, its full-length complementary strand, or a subsequence thereof, under low to very high stringency conditions. Molecules to which the probe hybridizes can be detected using, for example, X-ray film or any other detection means known in the art.

In one aspect, the nucleic acid probe is the mature polypeptide coding sequence of SEQ ID NO: 3. In another aspect, the nucleic acid probe is nucleotides 55 to 1419 of SEQ ID NO: 3. In another aspect, the nucleic acid probe is a polynucleotide that encodes the polypeptide of SEQ ID NO: 2 or a fragment thereof. In another aspect, the nucleic acid probe is SEQ ID NO: 3.

In another aspect, the parent is encoded by a polynucleotide having a sequence identity to the mature polypeptide coding sequence of SEQ ID NO: 3 of at least 60%, e.g., at least 65%, at least 70%, at least 75%, at least 80%, at least 85%, at least 90%, at least 95%, at least 96%, at least 97%, at least 98%, at least 99%, or 100%, which encodes a polypeptide having glucoamylase activity. In one aspect, the mature polypeptide coding sequence is nucleotides 55 to 1722 of SEQ ID NO: 3. In one aspect, the mature polypeptide coding sequence is nucleotides 55 to 1419 of SEQ ID NO: 3. In an embodiment, the parent is encoded by a polynucleotide comprising or consisting of SEQ ID NO: 3.

The parent may be obtained from microorganisms of any genus. For purposes of the present invention, the term "obtained from" as used herein in connection with a given source shall mean that the parent encoded by a polynucleotide is produced by the source or by a cell in which the polynucleotide from the source has been inserted. In one aspect, the parent is secreted extracellularly.

The parent may be a fungal glucoamylase. For example, the parent may be a filamentous fungal glucoamylase. In a preferred aspect, the parent glucoamylase is derived from a strain of the genus *Trametes*, especially the species *Trametes cingulata* shown in SEQ ID No: 2 herein, e.g., the glucoamylase of SEQ ID NO: 2 or the mature polypeptide thereof. The parent enzyme may be the one disclosed as SEQ ID NO: 2 in WO 2006/069289 (Novozymes) hereby incorporated by reference. More specifically the parent mature glucoamylase has the amino acid sequence shown in amino acids 1 to 556 of SEQ ID NO: 2; or the *E. coli* strain deposited at DSMZ and given the no. DSM 17106. Deposited strain DSM 17106 harbors plasmid HUda595 comprising a sequence identical to SEQ ID NO: 3.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc,) using the above-mentioned probes. Techniques for isolating microorganisms and DNA directly from natural habitats are well known in the art. The polynucleotide encoding a parent may then be derived by similarly screening a genomic or cDNA library of another microorganism or mixed DNA sample. Once a polynucleotide encoding a parent has been detected with a probe(s), the polynucleotide may be isolated or cloned by utilizing techniques that are known to those of ordinary skill in the art (see, e.g., Sambrook et al., 1989, supra).

The parent may be a hybrid polypeptide in which a portion of one polypeptide is fused at the N-terminus or the C-terminus of a portion of another polypeptide.

The parent also may be a fused polypeptide or cleavable fusion polypeptide in which one polypeptide is fused at the N-terminus or the C-terminus of another polypeptide. A fused polypeptide is produced by fusing a polynucleotide encoding one polypeptide to a polynucleotide encoding another polypeptide. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987;

Carter et al., 1989, *Proteins: Structure, Function, and Genetics* 6: 240-248; and Stevens, 2003, *Drug Discovery World* 4: 35-48.

Preparation of Variants

The present invention also relates to methods for obtaining a variant having glucoamylase activity, comprising: (a) introducing into a parent glucoamylase an alteration at one or more (several) corresponding to positions 20; 90; 121; 369; 397; 405; 408; 466; 470; 474; 539; and 552 of the mature polypeptide of SEQ ID NO: 2, wherein the variant has glucoamylase activity; and (b) recovering the variant. The alteration is preferably a substitution.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (several) mutations are created at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein olgionucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cRyIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases).

A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell, including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida*, *Hansenula*, *Kluyveromyces*, *Pichia*, *Saccharomyces*, *Schizosaccharomyces*, or *Yarrowia* cell such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising a variant of the present invention. Preferably, the compositions are enriched in such a variant. The term "enriched" means that the glucoamylase activity of the composition has been increased, e.g., with an enrichment factor of 1.1.

The composition may comprise a variant of the invention, preferably as the major enzymatic component, e.g., a mono-component composition. Alternatively, the composition may comprise multiple enzymatic activities, such as especially alpha-amylase activity and protease activity In a preferred embodiment the composition of the invention comprises a variant of the invention and an alpha-amylase, preferably a fungal alpha-amylase, such as a fungal acid alpha-amylase.

Fungal alpha-amylases include alpha-amylases derived from a strain of the genus *Aspergillus*, such as, *Aspergillus oryzae, Aspergillus niger* and *Aspergillis kawachii* alpha-amylases.

A preferred acidic fungal alpha-amylase is a Fungamyl-like alpha-amylase which is derived from a strain of *Aspergillus oryzae*. According to the present invention, the term "Fungamyl-like alpha-amylase" indicates an alpha-amylase which exhibits a high identity, i.e. at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *Aspergillus niger* disclosed as "AMYA_ASPNG" in the Swiss-prot/TeEMBL database under the primary accession no. P56271 and described in WO 89/01969 (Example 3—incorporated by reference). An acid fungal alpha-amylase derived from *Aspergillus niger* is referred to as "SP288" is available from Novozymes NS, Denmark.

The fungal alpha-amylase may also be a wild-type enzyme comprising a starch-binding domain (SBD) and an alpha-amylase catalytic domain (i.e., none-hybrid), or a variant thereof.

In a preferred embodiment the alpha-amylase is derived from *Aspergillus kawachii* and disclosed by Kaneko et al., 1996, *J. Ferment. Bioeng.* 81:292-298, "Molecular-cloning and determination of the nucleotide-sequence of a gene encoding an acid-stable alpha-amylase from *Aspergillus kawachii*."; and further as EMBL:#AB008370.

In an embodiment the wild-type alpha-amylase is derived from a strain of *Aspergillus kawachii*. Other contemplated wild-type alpha-amylases include those derived from a strain of the genera *Rhizomucor* and *Meripilus*, preferably a strain of *Rhizomucor pusillus* (WO 2004/055178 hereby incorporated by reference) or *Meripilus giganteus*.

In a preferred embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. patent application No. 60/638,614, including Fungamyl variant with catalytic domain JA118 and *Athelia rolfsii* SBD (SEQ ID NO:100 in U.S. 60/638,614), *Rhizomucor pusillus* alpha-amylase with *Athelia rolfsii* AMG linker and SBD (SEQ ID NO:101 in U.S. 60/638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO:102 in U.S. 60/638,614). Other specifically contemplated hybrid alpha-amylases are any of the ones listed in Tables 3, 4, 5, and 6 in Example 4 in U.S. application Ser. No. 11/316,535 and WO 2006/069290 (hereby incorporated by reference).

Other specific examples of contemplated hybrid alpha-amylases include those disclosed in WO 2005/03311, including those disclosed in Table 4 and 5 on page 33, such as *Aspergillus niger* alpha-amylase with *Aspergillus kawachii* linker and starch binding domain (JA001) and *Aspergillus niger* alpha-amylase with *Athelia rolfsii* linker and/or starch binding domain (JA004 or JA0011).

Contemplated are also alpha-amylases which exhibit a high identity to any of above mention alpha-amylases, i.e., at least 70%, at least 75%, at least 80%, at least 85%, at least 90%, at least 95%, at least 96%, at least 97%, at least 98%, at least 99% or even 100% identity to the mature enzyme sequences.

In an embodiment the alpha-amylase is derived from *Rhizomucor pusillus* and further has a SBD, such as a linker and a SBD at the C-terminal.

In a preferred embodiment the alpha-amylase is the *Rhizomucor pusillus* alpha-amylase with *Aspergillus niger* glucoamylase linker and SBD, such as the one disclosed in Table 5 as V039 in Table 5 in WO 2006/069290 (hereby incorporated by reference) or SEQ ID NO: 4 herein.

The ratio between acid fungal alpha-amylase activity (AFAU) and glucoamylase activity (AGU) (i.e., AFAU per AGU) may in an embodiment of the invention be between 0.1 and 100, in particular between 2 and 50, such as in the range from 10-40.

A composition may also comprise a protease. In a preferred embodiment the protease is an acid protease of microbial origin, preferably of fungal or bacterial origin. In an embodiment the protease is an acid fungal protease. In another embodiment the protease is a metallo protease.

Preferred proteases are acidic proteases, i.e., proteases characterized by the ability to hydrolyze proteins under acidic conditions below pH 7.

Contemplated acid fungal proteases include fungal proteases derived from *Aspergillus, Mucor, Rhizopus, Candida, Coriolus, Endothia, Enthomophtra, Irpex, Penicillium, Sclerotium* and *Thermoascus, Torulopsis*. Especially contemplated are proteases derived from *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), *Aspergillus awamori* (Hayashida et al., 1977, *Agric. Biol. Chem.* 42(5): 927-933, *Aspergillus aculeatus* (WO 95/02044), or *Aspergillus oryzae*, such as the pepA protease; and acidic proteases from *Mucor pusiflus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No. P06832. Also contemplated are the proteases having at least 90% identity to amino acid sequence obtainable at Swissprot as Accession No. P06832 such as at least 92%, at least 95%, at least 96%, at least 97%, at least 98%, or particularly at least 99% identity.

Further contemplated are the metallo proteases having at least 90% identity to amino acid sequence disclosed as SEQ ID NO: 2 in the WO 2003/048353, or SEQ ID NO: 2 herein, derived from *Thermoascus auranticus*, especially *Thermoascus auranticus* CGMCC No. 0670, such as at least 92%, at least 95%, at least 96%, at least 97%, at least 98%, or at least 99%, or 100% identity to SEQ ID NO: 2 herein.

Also contemplated are papain-like proteases such as proteases within E.C. 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

In an embodiment the protease is a protease preparation derived from a strain of *Aspergillus*, such as *Aspergillus oryzae*. In another embodiment the protease is derived from a strain of *Rhizomucor*, preferably *Rhizomucor mehei*. In another contemplated embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor mehei*.

Aspartic acid proteases are described in, for example, Hand-book of Proteolytic Enzymes, Edited by A. J. Barrett, N. D. Rawlings and J. F. Woessner, Aca-demic Press, San Diego, 1998, Chapter 270). Suitable examples of aspartic acid protease include, e.g., those disclosed in R. M. Berka et al. Gene, 96, 313 (1990)); (R. M. Berka et al. Gene, 125, 195-198 (1993)); and Gomi et al. Biosci. Biotech. Biochem. 57, 1095-1100 (1993), which are hereby incorporated by reference.

In an embodiment the composition comprises:
i) a glucoamylase variant of the invention;
ii) an acid fungal alpha-amylase derived from *Rhizomucor*, such as *Rhizomucor pusillus*.

In a specific embodiment the composition comprises:
i) a glucoamylase variant of the invention;
ii) an acid fungal alpha-amylase derived from *Rhizomucor pusillus* with *Aspergillus niger* glucoamylase linker and SBD, such as the one disclosed in Table 5 as V039 in Table 5 in WO 2006/069290 (hereby incorporated by reference) and show in SEQ ID NO: 4;

iii) optionally a protease derived from *Thermoascus auranticus*.

The composition of the invention may be prepared in accordance with methods known in the art and may be in the form of a liquid or a dry composition. For instance, the composition may be in the form of a granulate or a microgranulate. The variant may be stabilized in accordance with methods known in the art.

Methods/Processes of Using Glucoamylase Variants of the Invention—Industrial Applications The variants of the present invention possess valuable properties allowing for a variety of industrial applications. In particular, the variants may be used in starch conversion processes ethanol production, and brewing, such as beer making.

Uses according to the invention include starch conversion of starch to e.g., syrup and fermentation products, including ethanol and beverages. Examples of processes where a glucoamylase variant of the invention may be used include the ones described in: WO 2007/134207, WO 2006/069289, WO 2006/069290, WO 2004/081193, WO 2004/080923, WO 2003/66816, WO 2003/66826, WO 2003/029449, and WO 1992/20777 which are hereby all incorporated by reference.

Also contemplated are compositions for starch conversion purposes, which may beside the variant of the invention also comprise one or more alpha-amylases, pullulanases, and other glucoamylases.

Further, the variants are particularly useful in the production of sweeteners and ethanol (see, e.g., WO 2004/080923 or WO2004/081193, which are hereby incorporated by reference), such as fuel, drinking and industrial ethanol, from granular starch.

In one aspect, the invention relates to processes of producing syrup comprising:

(a) grinding a starch-containing material that has not been wet milled to produce a ground starch-containing material;

(b) liquefying the ground starch-containing material with an alpha-amylase to produce a liquefied starch-containing material comprising a dextrin;

(c) saccharifying the liquefied starch-containing material with a glucoamylase variant or a composition of the invention to produce a syrup.

The process may further comprise refining, conversion and/or recovery of the syrup.

Processes for Producing Fermentation Products and Sugars from Gelatinized Starch-Containing Materials A glucoamylase variant or composition of the invention may be used in a process of producing a fermentation product from a gelatinized starch-containing material. In particular, the present invention relates to a process of producing a fermentation product, comprising:

(a) grinding a starch-containing material that has not been wet milled to produce a ground starch-containing material;

(b) liquefying the ground starch-containing material with an alpha-amylase to produce a liquefied starch-containing material comprising a dextrin;

(c) saccharifying the liquefied starch-containing material with a glucoamylase variant of the invention to produce a saccharified material comprising a sugar; and (d) fermenting the saccharified material with a fermenting organism.

In another embodiment, the present invention relates to a process of producing a sugar, comprising:

(a) grinding a starch-containing material that has not been wet milled to produce a ground starch-containing material;

(b) liquefying the ground starch-containing material with an alpha-amylase to produce a liquefied starch-containing material comprising a dextrin; and (c) saccharifying the liquefied starch-containing material to a sugar with a glucoamylase variant of the invention to produce a saccharified material comprising a sugar.

Treatment Prior to Liquefaction

In an embodiment, the starch-containing material is treated prior to liquefaction. This treatment may be carried out at any pH and temperature suitable for enzyme activity. In an embodiment, the temperature is in the range of 20-75° C., e.g., 20-65° C. or 40-60° C.; the pH is in the range of 4.5-6.5; and the period of time is in the range of 5 minutes-2 hours, e.g., 5 minutes-1 hour.

Liquefaction

During a typical liquefaction, the long-chained starch is degraded into branched and linear shorter units (maltodextrins) by an alpha-amylase. Liquefaction is carried out in the presence of an alpha-amylase, preferably a bacterial alpha-amylase and/or acid fungal alpha-amylase. In an embodiment, a pullulanase, isoamylase, and and/or phytase is added during liquefaction.

Liquefaction may be carried out as a single-step liquefaction at 85° C. for 1-4 hours. Liquefaction also may be carried out as a three-step hot slurry process. The slurry is heated to between 60-95° C. (e.g., 77-86° C., 80-85° C., or 83-85° C.) and an alpha-amylase(s) is (are) added to initiate liquefaction (thinning). Then the slurry may be jet-cooked at a temperature of 95-140° C., e.g., 105-125° C., for about 1-15 minutes, e.g., about 3-10 minutes, especially around 5 minutes. The slurry is cooled to 60-95° C. and more alpha-amylase is added to finalize the hydrolysis (secondary liquefaction). The liquefaction process is usually carried out at a pH of 4.5-6.5, in particular at a pH from 5 to 6. All of the alpha-amylases may be added as a single dose, e.g., before jet cooking. After liquefaction, the liquefied starch will have a "dextrose equivalent" (DE) of 8-15.

In order to ensure optimal enzyme stability during liquefaction, 1 mM of calcium is optionally added (to provide about 40 ppm free calcium ions).

Saccharification

Saccharification may be carried out using conditions well known in the art with a glucoamylase variant of the invention or a composition of the invention. For instance, a full saccharification step may last from about 24 to about 72 hours, however, it is also common to do a pre-saccharification of typically 40-90 minutes at a temperature between 30-65° C., typically about 60° C., followed by complete saccharification before initiation of fermentation. Saccharification is typically carried out at a temperature in the range of 20-75° C., e.g., 25-65° C. and 40-70° C., typically around 60° C., and at a pH between about 4 and 5, normally at about pH 4.5.

In an embodiment, saccharification results in the production of maltose. In another embodiment, saccharification results in the production of glucose. The glucose may be converted to fructose. The sugars may be recovered by methods well known in the art.

Simultaneous Saccharification and Fermentation (SSF)

Saccharification and fermentation may be carried out simultaneously. In this embodiment, there is no holding stage for the saccharification, meaning that a fermenting organism, such as yeast, and enzyme(s) are added together. SSF is typically carried out at conditions (e.g., temperature and/or pH) suitable, preferably optimal, for the fermenting organism(s) in question, e.g., a temperature of 20-40° C., e.g., 26-34° C., preferably around 32° C., when the fermentation organism is yeast, such as a strain of *Saccharomyces cerevisiae*, and the fermentation product is ethanol.

Other fermentation products may be fermented at conditions and temperatures well known to persons skilled in the art, suitable for the fermenting organism in question. According to the invention the temperature may be adjusted up or down during fermentation.

Fermentation

Different kinds of fermenting organisms may be used for fermenting sugars derived from a starch-containing material. Fermentation is conventionally carried out using yeast, such as *Saccharomyces cerevisae*, as the fermenting organism. However, bacteria and filamentous fungi may also be used as fermenting organisms. Some bacteria have a higher fermentation temperature optimum than, e.g., *Saccharomyces cerevisae*. Therefore, fermentations may in such cases be carried out at temperatures as high as 75° C., e.g., between 40-70° C., such as between 50-60° C. However, bacteria with a significantly lower temperature optimum down to around room temperature (around 20° C.) are also known.

For ethanol production using yeast, the fermentation may be performed for 24 to 96 hours, in particular for 35 to 60 hours. In an embodiment the fermentation is carried out at a temperature between 20 to 40° C., preferably 26 to 34° C., in particular around 32° C. The temperature may be adjusted up or down during fermentation. In an embodiment the pH is from pH 3 to 7, e.g., 3.5 to 6, 4 to 5, and around 5.

Other fermentation products may be fermented at temperatures known to the skilled person in the art to be suitable for the fermenting organism in question.

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

The methods or processes of the invention may be performed as a batch or as a continuous process. Fermentations of the invention may be conducted in an ultrafiltration system wherein the retentate is held under recirculation in the presence of solids, water, and the fermenting organism, and wherein the permeate is the desired fermentation product containing liquid. Equally contemplated are methods/processes conducted in continuous membrane reactors with ultrafiltration membranes and where the retentate is held under recirculation in presence of solids, water, and the fermenting organism(s) and where the permeate is the fermentation product containing liquid.

After fermentation the fermenting organism may be separated from the fermented slurry and recycled.

Processes for Producing Fermentation Products from Un-Gelatinized Starch-Containing Material A glucoamylase variant or composition of the invention may be used in a process of producing a fermentation product from a starch-containing material without gelatinization (often referred to as "without cooking") of the starch-containing material. In this embodiment, the process includes grinding a starch-containing material that has not been wet milled (e.g., dry milled); and saccharifying starch-containing material, e.g., granular starch, below the initial gelatinization temperature, preferably in the presence of a glucoamylase variant or composition of the invention, preferably comprising a glucoamylase variant of the invention and an alpha-amylase, to produce sugars that can be fermented into the desired fermentation product by a suitable fermenting organism.

Accordingly, in this aspect the invention relates to processes of producing a fermentation product from starch-containing material comprising the steps of:

(a) grinding a starch-containing material that has not been wet milled to produce a ground starch-containing material;

(b) saccharifying the ground starch-containing material with an alpha-amylase and a saccharifying enzyme at a temperature below the initial gelatinization temperature of the starch-containing material to produce a saccharified material comprising a sugar; and (c) fermenting the saccharified material with a fermenting organism.

In a preferred embodiment steps (b) and (c) are carried out simultaneously (i.e., one-step fermentation).

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466.

The process of this aspect of the invention is conducted at a temperature below the initial gelatinization temperature. When saccharification is carried out separately from fermentation, the temperature typically lies in the range between 30-75° C., preferably in the range from 45-60° C. The following separate fermentation step is then carried out at a temperature suitable for the fermenting organism, which typically is in the range between 25-40° C. when the fermenting organism is yeast.

In a preferred embodiment saccharification and fermentation are carried out as a simultaneous saccharification and fermentation process. In such embodiment the process is typically carried out at a temperature between 25° C. and 40° C., such as between 29° C. and 35° C., such as between 30° C. and 34° C., such as around 32° C., when the fermenting organism is yeast. One skilled in the art can easily determine which process conditions are suitable.

In an embodiment fermentation is carried out so that the sugar level, such as glucose level, is kept at a low level, such as below 6 wt. %, below about 3 wt. %, below about 2 wt. %, below about 1 wt. %, below about 0.5 wt. %, below 0.25 wt. %, or below about 0.1 wt. %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt. %, such as below about 0.2 wt. %.

The process of the invention may be carried out at a pH from about 3 and 7, preferably from pH 3.5 to 6, or more preferably from pH 4 to 5.

Fermentation Medium

The phrase "fermentation media" or "fermentation medium" refers to the environment in which fermentation is carried out and comprises the fermentation substrate, that is, the carbohydrate source that is metabolized by the fermenting organism(s), and may include the fermenting organism(s).

The fermentation medium may comprise nutrients and growth stimulator(s) for the fermenting organism(s). Nutrient and growth stimulators are widely used in the art of fermentation and include nitrogen sources, such as ammonia, vitamins and minerals, or combinations thereof.

Following fermentation, the fermentation media or fermentation medium further comprises the fermentation product.

Fermenting Organisms

The term "fermenting organism" refers to any organism, including bacterial and fungal organisms, including yeast and filamentous fungi, suitable for producing a desired fermentation product. Suitable fermenting organisms according to the invention are able to ferment, i.e., convert fermentable sugars, such as arabinose, fructose, glucose, maltose, mannose, or xylose, directly or indirectly into the desired fermentation product.

Examples of fermenting organisms include fungal organisms such as yeast. Preferred yeast includes strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida utilis*, *Candida arabinofermentans*, *Candida diddensii*, *Candida sonorensis*, *Candida shehatae*, *Candida tropicalis*, or *Candida boidinii*. Other fermenting organisms include strains of *Hansenula*, in particular *Hansenula polymorpha* or *Hansenula anomala*; *Kluyveromyces*, in particular *Kluyveromyces fragilis* or *Kluyveromyces marxianus*; and *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of Zymobacter, in particular *Zymobactor palmae*, strains of *Klebsiella*, in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes* and strains of *Thermoanaerobacter*, in particular *Thermoanaerobacter* BG1L1 (*Appl. Microbiol. Biotech.* 77: 61-86) and *Thermoanarobacter ethanolicus*, *Thermoanaerobacter thermosaccharolyticum*, or *Thermoanaerobacter mathranii*. Strains of *Lactobacillus* as well as strains of *Corynebacterium glutamicum*R, *Bacillus thermoglucosidaisus*, and *Geobacillus thermoglucosidasius* may also be used.

In an embodiment the fermenting organism is a C6 sugar fermenting organism, such as a strain of, e.g., *Saccharomyces cerevisiae*.

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Yeast is the preferred fermenting organism for ethanol fermentation. Preferred are strains of *Saccharomyces*, especially strains of *Saccharomyces cerevisiae*, preferably strains which are resistant towards high levels of ethanol, i.e., up to, e.g., about 10, 12, 15 or 20 vol. % or more ethanol.

Commercially available yeast include, e.g., RED START™ and ETHANOL RED™ yeast (available from Fermentis/Lesaffre, USA), FALI (available from Fleischmann's Yeast, USA), SUPERSTART and THERMO-SACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

According to the invention the fermenting organism capable of producing a desired fermentation product from fermentable sugars, including arabinose, fructose, glucose, maltose, mannose, or xylose, is preferably grown under precise conditions at a particular growth rate. When the fermenting organism is introduced into/added to the fermentation medium the inoculated fermenting organism passes through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

Fermentation Products

The term "fermentation product" means a product produced by a method or process including fermenting using a fermenting organism. The fermentation product can be, without limitation, an alcohol (e.g., arabinitol, butanediol, n-butanol, isobutanol, ethanol, ethylene glycol, glycerin, glycerol, methanol, 1,3-propanediol [propylene glycol], sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., carbon dioxide ($CO_2$), carbon monoxide (CO), hydrogen ($H_2$), and methane); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

A preferred fermentation product is an alcohol. The alcohol, preferably ethanol, may be used as fuel or, in the case of ethanol, may also be used as potable ethanol.

Recovery

Subsequent to fermentation, the fermentation product may be separated from the fermentation medium by methods well known in the art, e.g., by distillation.

In particular, the fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

Starch-Containing Materials

Any suitable starch-containing starting material, including granular starch (raw uncooked starch), may be used according to the present invention. The starting material is generally selected based on the desired fermentation product. Examples of starch-containing starting materials, suitable for use in methods or processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley.

Brewing

A glucoamylase variant of the invention can also be used in a brewing process, such as a beer-making process. The glucoamylases of the invention is added in effective amounts which can be easily determined by the skilled person in the art. For instance, in the production of "low carb" or super attenuated beers, a higher proportion of alcohol and a lower amount of residual dextrin are desired. These beers are formulated using exogenous enzymes compositions comprising enzyme activities capable of debranching the limit dextrins. A glucoamylase variant of the invention may be applied to reduce the content of limit dextrins as well as hydrolyzing the alpha-1,4 bonds.

Further details on how to carry out liquefaction, saccharification, fermentation, distillation, and recovery of ethanol are well known to the skilled person.

According to the process provided herein, the saccharification and fermentation may be carried out simultaneously or separately.

List of Embodiments

1. A variant of a parent glucoamylase comprising an alteration at one or more (several) positions corresponding to positions;
20, 90, 121, 369, 397, 405, 408, 466, 470, 474, 539, and 552 of the mature polypeptide of SEQ ID NO: 2 wherein each alteration is independently a substitution and the variant has glucoamylase activity.
2. The variant of embodiment 1 comprising an alteration at a position corresponding to position 20 of the mature polypeptide of SEQ ID NO: 2 wherein the alteration is a substitution and the variant has glucoamylase activity.
3. The variant of embodiment 1 comprising an alteration at a position corresponding to position 90 of the mature polypeptide of SEQ ID NO: 2 wherein the alteration is a substitution and the variant has glucoamylase activity.
4. The variant of embodiment 1 comprising an alteration at a position corresponding to position 121 of the mature polypeptide of SEQ ID NO: 2 wherein the alteration is a substitution and the variant has glucoamylase activity.
5. The variant of embodiment 1 comprising an alteration at a position corresponding to position 369 of the mature polypeptide of SEQ ID NO: 2 wherein the alteration is a substitution and the variant has glucoamylase activity.
6. The variant of embodiment 1 comprising an alteration at a position corresponding to position 397 of the mature polypeptide of SEQ ID NO: 2 wherein the alteration is a substitution and the variant has glucoamylase activity.
7. The variant of embodiment 1 comprising an alteration at a position corresponding to position 405 of the mature polypeptide of SEQ ID NO: 2 wherein the alteration is a substitution and the variant has glucoamylase activity.
8. The variant of embodiment 1 comprising an alteration at a position corresponding to position 408 of the mature polypeptide of SEQ ID NO: 2 wherein the alteration is a substitution and the variant has glucoamylase activity.
9. The variant of embodiment 1 comprising an alteration at a position corresponding to position 466 of the mature polypeptide of SEQ ID NO: 2 wherein the alteration is a substitution and the variant has glucoamylase activity.
10. The variant of embodiment 1 comprising an alteration at a position corresponding to position 470 of the mature polypeptide of SEQ ID NO: 2 wherein the alteration is a substitution and the variant has glucoamylase activity.
11. The variant of embodiment 1 comprising an alteration at a position corresponding to position 474 of the mature polypeptide of SEQ ID NO: 2 wherein the alteration is a substitution and the variant has glucoamylase activity.
12. The variant of embodiment 1 comprising an alteration at a position corresponding to position 539 of the mature polypeptide of SEQ ID NO: 2 wherein the alteration is a substitution and the variant has glucoamylase activity.
13. The variant of embodiment 1 comprising an alteration at a position corresponding to position 552 of the mature polypeptide of SEQ ID NO: 2 wherein the alteration is a substitution and the variant has glucoamylase activity.
14. The variant of any of embodiments 1-13, wherein the parent glucoamylase is
   a. a polypeptide having at least 60% sequence identity to the mature polypeptide of SEQ ID NO: 2;
   b. a polypeptide encoded by a polynucleotide that hybridizes under low stringency conditions with (i) the mature polypeptide coding sequence of SEQ ID NO: 3, (ii) the genomic DNA sequence comprising the mature polypeptide coding sequence of SEQ ID NO: 3 or (iii) the full-length complementary strand of (i) or (ii);
   c. a polypeptide encoded by a polynucleotide having at least 60% identity to the mature polypeptide coding sequence of SEQ ID NO: 3; or
   d. a fragment of the mature polypeptide of SEQ ID NO: 2, which has glucoamylase activity.
15. The variant of any of embodiments 1-14, wherein the parent glucoamylase has at least 60%, e.g., at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO: 2.
16. The variant of any of embodiments 1-15, wherein the parent glucoamylase is encoded by a polynucleotide that hybridizes under low stringency conditions, medium stringency conditions, medium-high stringency conditions, high stringency conditions, and very high stringency conditions with (i) the mature polypeptide coding sequence of SEQ ID NO: 3 or (ii) the full-length complementary strand of (i).
17. The variant of any of embodiments 1-16, wherein the parent glucoamylase is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the mature polypeptide coding sequence of SEQ ID NO: 3.
18. The variant of any of embodiments 1-17, wherein the parent glucoamylase comprises or consists of the mature polypeptide of SEQ ID NO: 2.
19. The variant of any of embodiments 1-5, wherein the parent glucoamylase is a fragment of the mature polypeptide of SEQ ID NO: 2 wherein the fragment has glucoamylase activity.
20. The variant of any of embodiments 1-7, which variant has at least 60%, e.g., at least 65%, at least 70%, at least 75%, at least 80%, at least 85%, at least 90%, at least 95% identity, at least 96%, at least 97%, at least 98%, at least 99%, but less than 100%, sequence identity to the amino acid sequence of the parent glucoamylase.
21. The variant of any of embodiments 1-20, which variant has at least 60%, e.g., at least 65%, at least 70%, at least 75%, at least 80%, at least 85%, at least 90%, at least 95%, at least 96%, at least 97%, at least 98%, and at least 99%, but less than 100% sequence identity to the mature polypeptide of SEQ ID NO: 2.
22. The variant of any of embodiments 1-21, wherein the variant consists of 455 to 556, such as 463 to 556, 500 to 545, 510 to 535, 520 to 525 amino acids.

23. The variant of any of embodiments 1-22, wherein the number of alterations, preferably substitutions, is 1-20, e.g., 1-10 and 1-5, such as 1, 2, 3, 4, 5, 6, 7, 8, 9 or 10 alterations compared to SEQ ID NO: 2.

24. The variant of any of embodiments 1-23, which comprises one or more (several) of the following substitutions in SEQ ID NO: 2 or in one or more corresponding positions selected from the group consisting of: V20L, I90G, A121S, Y369F, Y397T, A405R, Y408F, T466S, Q470T, V474K, N539T and N552T or Y.

25. The variant of any of embodiments 1-24, wherein the variant has one or more (several) of the following substitutions: V20L; Y369F and N552T or Y.

26. The variant of any of embodiments 1-25, wherein the variant is one of the following: V20L+Y369F+N552T; Y369F+N539T; V20L+Y369F+Q470T+V474K; V20L+Y369F; V20L+Y397T+Y408F; Y397T+N539T; Y397T+N552Y; I90G+Y369F; T466S+N552Y; V20L+I90G; A121S+Y408F; Y397T+Y408F+N552T; and A405R+T466S.

27. The variant of any of embodiments 1-26, wherein the variant has increased ethanol yields compared to the parent glucoamylase in a conventional ethanol process and/or in a raw starch hydrolysis ethanol process.

28. A polynucleotide encoding the variant of any of embodiments 1-27.

29. A nucleic acid construct comprising the polynucleotide of embodiment 28.

30. An expression vector comprising the polynucleotide of embodiment 28.

31. A host cell comprising the polynucleotide of embodiment 28.

32. A method of producing a variant of a parent glucoamylase, comprising:
 a. cultivating the host cell of embodiment 31 under conditions suitable for the expression of the variant; and
 b. recovering the variant.

33. A transgenic plant, plant part or plant cell transformed with the polynucleotide of embodiment 28.

34. A method of producing a variant of any of embodiments 1-27, comprising:
 a. cultivating a transgenic plant or a plant cell comprising a polynucleotide encoding the variant under conditions conducive for production of the variant; and
 b. recovering the variant.

35. A composition comprising a glucoamylase variant of any of embodiments 1-27.

36. The composition of embodiment 35, further comprising an alpha-amylase and/or a protease.

37. The composition of embodiment 36, wherein the alpha-amylase is an acid alpha-amylase, such as a fungal acid alpha-amylase.

38. The composition of any of embodiments 35-37, wherein the composition comprises:
 i) a variant of any of embodiments 1-27;
 ii) an acid fungal alpha-amylase derived from *Rhizomucor*, such as *Rhizomucor pusillus*.

39. The composition of embodiments 38, wherein *Rhizomucor pusillus* alpha-amylase has SBD, such as a linker and a SBD.

40. The composition of embodiment 38 or 39, wherein the alpha-amylase is the with *Rhizomucor pusillus* alpha-amylase with *Aspergillus niger* glucoamylase linker and SBD, such as the one disclosed in Table 5 as V039 in Table 5 in WO 2006/069290 (hereby incorporated by reference) or SEQ ID NO: 4 herein.

41. The composition of any of embodiments 35-40, wherein the protease is a metallo protease, such as one having at least 90%, such as at least 92%, at least 95%, at least 96%, at least 97%, at least 98%, at least 99%, or 100% identity to the mature part of the amino acid sequence disclosed as SEQ ID NO: 2 in the WO 2003/048353, such as a metallo protease derived from *Thermoascus auranticus*, especially *Thermoascus auranticus* CGMCC No. 0670.

42. The composition of any of embodiments 35-41, wherein the composition comprises:
 i) a glucoamylase of any of embodiments 1-27;
 ii) an acid fungal alpha-amylase derived from *Rhizomucor pusillus* with *Aspergillus niger* glucoamylase linker and SBD, such as the one disclosed in Table 5 as V039 in Table 5 in WO 2006/069290 (hereby incorporated by reference);
 iii) optionally a protease derived from *Thermoascus auranticus*.

43. A process of producing a fermentation product, comprising:
 (a) grinding a starch-containing material that has not been wet milled to produce a ground starch-containing material;
 (b) liquefying the ground starch-containing material with an alpha-amylase to produce a liquefied starch-containing material comprising a dextrin;
 (c) saccharifying the liquefied starch-containing material with a glucoamylase variant of any of embodiments 1-27 or a composition of any of embodiments 35-42 to produce a saccharified material comprising a sugar; and
 (d) fermenting the saccharified material with a fermenting organism.

44. A process of producing a fermentation product comprising:
 (a) grinding a starch-containing material that has not been wet milled to produce a ground starch-containing material;
 (b) saccharifying the ground starch-containing material with a glucoamylase variant of any if embodiments 1-27 or a composition of any of embodiments 35-42 at a temperature below the initial gelatinization temperature of the starch-containing material to produce a saccharified material comprising a sugar; and
 (c) fermenting the saccharified material with a fermenting organism.

45. A process of producing syrup comprising:
 (a) grinding a starch-containing material that has not been wet milled to produce a ground starch-containing material;
 (b) liquefying the ground starch-containing material with an alpha-amylase to produce a liquefied starch-containing material comprising a dextrin;
 (c) saccharifying the liquefied starch-containing material with a glucoamylase variant of any of embodiments 1-27 or a composition of any of embodiments 35-42 to produce a syrup.

46. The process of embodiment 45, further comprising refining, conversion and/or recovery of the syrup.

47. Use of a glucoamylase variant according to any of embodiments 1-27 or a composition of any of embodiments 35-42 in a starch conversion process.

48. Use of a glucoamylase of any of embodiments 1-27 or a composition of any of embodiments 35-42 for production of syrup and/or a fermentation product.

49. Use of embodiment 48, wherein the starting material is gelatinized starch-containing material.

50. Use of embodiment 48, wherein the starting material is un-gelatinized starch-containing material.

51. Use of a glucoamylase variant according to any one of embodiments 1-27 or a composition of any of embodiments 35-42 in a process for producing ethanol, such as fuel ethanol or potable ethanol.

52. Use of a glucoamylase variant according to any one of embodiments 1-27 or a composition of any of embodiments 35-42 in a brewing process for producing a beverage, such as beer.

Materials & Methods

Glucoamylases:

TcAMG: Glucoamylase derived from *Trametes cingulata* (TcAMG) disclosed in SEQ ID NO: 2 herein.

Alpha-Amylase:

Hybrid Alpha-Amylase A: Hybrid alpha-amylase consisting of *Rhizomucor pusillus* alpha-amylase with *Aspergillus niger* glucoamylase linker and SBD disclosed as V039 in Table 5 in WO 2006/069290 (Novozymes NS).

Yeast: Red Star™ available from Red Star/Lesaffre, USA

Corn: Finely ground yellow dent corn. The corn was obtained from Hawkeye Renewables of Iowa Falls, Iowa, USA (Example 1 "RSH fermentation"—experiments)

Corn Mash: Frozen corn mash obtained from Platinum Ethanol containing 30.38% dry solids (Example 1: "Conventional fermentation"—experiments).

Media and Reagents:

Chemicals used as buffers and substrates were commercial products of at least reagent grade.

Methods

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for *Bacillus*". John Wiley and Sons, 1990.

Glucoamylase Activity

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes NS, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes NS, Denmark, which folder is hereby included by reference.

Acid Alpha-Amylase Activity

When used according to the present invention the activity of any acid alpha-amylase may be measured in AFAU (Acid Fungal Alpha-amylase Units). Alternatively activity of acid alpha-amylase may be measured in AAU (Acid Alpha-amylase Units).

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard Conditions/Reaction Conditions:

Substrate: Soluble starch. Concentration approx. 20 g DS/L.

Buffer: Citrate, approx. 0.13 M, pH=4.2

Iodine solution: 40.176 g potassium iodide+0.088 g iodine/L

City water 15°-20° dH (German degree hardness)

pH: 4.2

Incubation temperature: 30° C.

Reaction time: 11 minutes

Wavelength: 620 nm

Enzyme concentration: 0.13-0.19 AAU/mL

Enzyme working range: 0.13-0.19 AAU/mL

The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in EP 0140410 B2, which disclosure is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

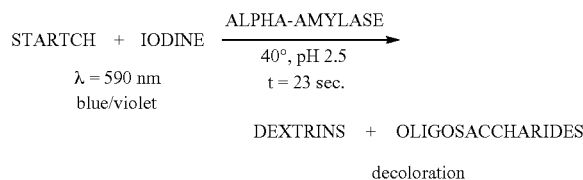

Standard Conditions/Reaction Conditions:
Substrate: Soluble starch, approx. 0.17 g/L
Buffer: Citrate, approx. 0.03 M
Iodine (I2): 0.03 g/L
$CaCl_2$: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL A folder EB-SM-0259.02/01 describing this analytical method in more detail is available upon request to Novozymes NS, Denmark, which folder is hereby included by reference.

Apha-Cyclodextrin Chromatography Method

TcAMG variants are purified by affinity chromatography on an alpha-cyclodextrin column using 50 mM acetate buffer, pH 4.5 for binding and the same buffer with 1% alpha-cyclodextrin for elution.

EXAMPLES

Example 1

Testing of Variants of Parent *Trametes cingulata* AMG (SEQ ID NO: 2) in Conventional SSF and Raw Starch Hydrolysis (RSH) Processes for Ethanol Production from Corn Variants of the *Trametes cingulata* glucoamylase (TcAMG) were created, purified and assayed for their performance in corn ethanol fermentation.

Enzymes:

The below *Trametes cingulata* AMG variants were purified from culture supernatants using an alpha-cyclodextrin chromatography method. The protein concentration was determined from A280 measurements, using the extinction coefficient calculated for each variant by the Mutantstat tool.

A blend of parent *Trametes cingulata* glucoamylase (TcAMG) and hybrid Alpha-Amylase A was also used as a benchmark.

V20L+Y369F+N552T;
Y369F+N539T;
V20L+Y369F+Q470T+V474K;
V20L+Y369F;
V20L+Y397T+Y408F;
Y397T+N539T;
Y397T+N552Y;
I90G+Y369F;
T466S+N552Y;
V20L+I90G;
A121S+Y408F;
Y397T+Y408F+N552T;
A405R+T466S.

"Raw Starch Hydrolysis Fermentation" Method (RSH Method)

*Trametes cingulata* AMG variants were assayed using a Raw Starch Hydrolysis method ("RSH fermentation" method). In this method the corn slurry is not cooked, but undergoes SSF with the use of a blend of parent *Trametes cingulata* glucoamylase (TcAMG) and hybrid alpha-amylase consisting of *Rhizomucor pusillus* alpha-amylase with *Aspergillus niger* glucoamylase linker and SBD (Hybrid Alpha-Amylase A).

For each set of RSH fermentations approximately 405 g of finely ground yellow dent corn was added to 595 g tap water and the dry solids (DS) level was determined to be about 35% DS. Urea and penicillin were added to a final concentration of 1000 ppm and 3 mg/L, respectively. The slurry was adjusted to pH 4.5 with 40% $H_2SO_4$. Approximately 5 g of this slurry was added to six replicate 15 mL tubes per treatment. Each tube was dosed with a glucoamylase at 0.089 mg EP/g DS and Hybrid Alpha-amylase A at 0.025 mg EP/g DS. After enzyme addition, 200 microL of yeast propagate (0.024 g Fermentis Ethanol Red® yeast, incubated overnight at 32° C. in 50 mL filtered liquefied corn mash and 5.1 microL *Aspergillus niger* AMG) was added to each tube.

Actual enzyme dosages were based on the exact weight of corn slurry in each tube according to the following formula:

$$Enz.\ dose(\mu L) = \frac{Final\ enz.\ dose\ (mg/g\ DS) \times Mash\ weight\ (g) \times Dry\ solids\ content\ (\%\ DS)}{Stock\ enzyme\ conc.\ (mg/mL) \times 1000}$$

Tubes were incubated in a temperature controlled room at 32° C. All tubes were vortexed at 24 and 48 hours; weight loss data were not collected. One sample was sacrificed for HPLC analysis at 24 hours, two at 48 hours, and three at 70 hours.

The HPLC preparation consisted of stopping the reaction by addition of 50 microL of 40% $H_2SO_4$, centrifuging for 10 min at 1462×g, and filtering through a 0.45 micro m filter. Samples were stored at 4° C. An Agilent™ 1100 HPLC system coupled with RI detector was used to determine ethanol and oligosaccharides concentrations. The separation column was a BioRad™ Aminex HPX-87H ion exclusion column (300 mm×7.8 mm).

Coefficients of variability for HPLC ethanol measurements ranged from 0.28-0.40%, resulting in a maximum standard error of 0.66 g/L for ethanol measurement from RSH fermentations.

"Conventional Fermentation" Method

Each glucoamylase variant was assayed at doses of 30, 45, and 60 micro g/g DS in a 30.38% DS corn mash. The performance for each glucoamylase variants (ethanol concentration after 54 hours of fermentation) was compared to purified TcAMG at doses of 30, 45, and 60 micro g/g DS and a high benchmark of "TcAMG-Hybrid Alpha-Amylase A" blend at a dose of 0.500 AGU/g DS.

Small-scale (~4 g industrial corn mash) fermentations were run using five replicates. Urea and penicillin were added to a final concentration of 1000 ppm and 3 mg/L, respectively. Enzymes were dosed to each tube according to the experimental concentrations described above. The formula below was used to calculate the volume of each enzyme stock solution to add to the fermentations:

$$\text{Enz. dose(ml)} = \frac{\text{Final }\textit{enz.}\text{ dose (mg/g }\textit{DS})\times \text{Mash weight (g)}\times \text{Solid content (\% }\textit{DS}/100)}{(\textit{Conc.}\text{ enzyme mg/ml})}$$

Water was added to all tubes so that the total added volume was 180 microLl per 5 g mash. Fermentation was then initiated by adding 100 microL of rehydrated yeast to all tubes. Each tube contained approximately 50 million cells/g DS of re-hydrated RedStar® yeast (5 g yeast+100 mL tap water, 30 min at 32° C.). Tubes were vortexed thoroughly and then weighed to record a 0-hour weight. Initial weights measured after yeast and enzyme addition were compared to expected weights as a check against dosing errors. Samples were then placed in a temperature-controlled room at 32° C. At several times during the fermentation the samples were vortexed for $CO_2$ liberation.

Finally, after 24 and 54 hours of fermentation, tubes from each treatment group were sacrificed for HPLC analysis of remaining sugar and ethanol concentration as described above.

The average coefficient of variability was 1.24% in weight loss and 0.94% for HPLC results, resulting in a standard error of 1.07 g/L for ethanol measurement from conventional fermentations. When data for the lowest dose were excluded, CVs were 0.93% and 0.66% for weight loss and HPLC, with a standard error of 0.83 g/I.

Table 1 displays the test results:

| | | wt | | | | | | | | | |
|---|---|---|---|---|---|---|---|---|---|---|---|
| Variant # Mutations | | P4M9 none | U33A3 V20L Y369F | U33A1 V20L Y369F Q470T V474K | U33A4 V20L Y369F N552T | U33AB V20L Y367T Y408F | U24YV I90G Y369F | U24XZ Y369F N539T | U24XY Y397T N539T | U33AA Y397T N552T | U24Z5 T466S N552Y |
| % of control in RSH fermentaion assay | | 100.0% | 100.7% | 101.7% | 100.8% | 100.7% | 100.6% | 100.5% | 100.2% | 101.0% | 100.9% |
| % of benchmark in conventional fermentation assay | 30 μg | 75.7% | 83.3% | 90.4% | 88.6% | 88.9% | 84.1% | 81.8% | 82.8% | 83.4% | 75.4% |
| | 45 μg | 93.1% | 94.3% | 94.4% | 95.0% | 92.6% | 94.0% | 95.6% | 96.3% | 93.8% | 92.7% |
| | 60 μg | 96.6% | 95.0% | 96.0% | 96.7% | 96.1% | 94.7% | 97.3% | 96.4% | 95.0% | 95.3% |

| | | wt | | | | |
|---|---|---|---|---|---|---|
| Variant # Mutations | | P4M9 none | U339R V20L I90G | U339U A121S Y408F | U33A6 Y397T Y408F N552T | U24Z1 A405R T466S |
| % of control in benchmark fermentation assay | | 100.0% | 100.2% | 100.7% | 100.5% | 100.3% |
| % of RSH in conventional fermentation assay | 30 μg | 75.7% | 84.6% | 82.1% | 77.8% | 88.0% |
| | 45 μg | 93.1% | 93.6% | 92.9% | 94.1% | 90.1% |
| | 60 μg | 96.6% | 95.3% | 94.0% | 95.5% | 90.6% |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A variant of a parent glucoamylase comprising an alteration at one or more positions corresponding to positions;
20, 90, 121, 369, 397, 405, 408, 466, 470, 474, 539, and 552
of amino acids 1 to 556 of SEQ ID NO: 2 wherein each alteration is independently a substitution and the variant has glucoamylase activity.

2. The variant of claim 1, wherein the parent glucoamylase is:
   a. a polypeptide having at least 85% sequence identity to amino acids 1 to 556 of SEQ ID NO: 2;
   b. a polypeptide encoded by a polynucleotide that hybridizes under low stringency conditions with (i) nucleotides 55 to 1722 of SEQ ID NO: 3, (ii) the genomic DNA sequence comprising nucleotides 55 to 1722 of SEQ ID NO: 3 or (iii) the full-length complementary strand of (i) or (ii);
   c. a polypeptide encoded by a polynucleotide having at least 85% identity to nucleotides 55 to 1722 of SEQ ID NO: 3.

3. The variant of claim 1, wherein the parent glucoamylase has at least 85% identity to amino acids 1 to 556 of SEQ ID NO: 2.

4. The variant of claim 1, wherein the parent glucoamylase is encoded by a polynucleotide that hybridizes under high stringency conditions, and very high stringency conditions with (i) nucleotides 55 to 1722 of SEQ ID NO: 3 or (ii) the full-length complementary strand of (i).

5. The variant of claim 1, wherein the parent glucoamylase is encoded by a polynucleotide having at least 85% sequence identity to nucleotides 55 to 1722 of SEQ ID NO: 3.

6. The variant of claim 1, wherein the number of alterations is 1-10 alterations compared to SEQ ID NO: 2.

7. The variant of claim 1, which comprises one or more of the following substitutions in SEQ ID NO: 2 or in one or more corresponding positions selected from the group consisting of: V20L, I90G, A121S, Y369F, Y397T, A405R, Y408F, T466S, Q470T, V474K, N539T, N552T and N552Y.

8. The variant of claim 1, wherein the variant has one or more of the following substitutions: V20L; Y369F, N552T and N552Y.

9. The variant of claim 1, wherein the variant is one of the following: V20L+Y369F+N552T; Y369F+N539T; V20L+Y369F+Q470T+V474K; V20L+Y369F; V20L+Y397T+Y408F; Y397T+N539T; Y397T+N552Y; I90G+Y369F; T466S+N552Y; V20L+I90G; A121S+Y408F; Y397T+Y408F+N552T; and A405R+T466S.

10. The variant of claim 1, wherein the variant has increased ethanol yields compared to the parent glucoamylase in a conventional ethanol process and/or in a raw starch hydrolysis ethanol process.

11. A composition comprising the glucoamylase variant of claim 1.

12. The composition of claim 11, wherein the composition further comprises:
   i) *Rhizomucor pusillus* acid fungal alpha-amylase with *Aspergillus niger* glucoamylase linker and starch-binding domain (SBD); and
   ii) optionally a *Thermoascus auranticus* protease.

13. A process of producing a fermentation product, comprising:
   (a) grinding a starch-containing material that has not been wet milled to produce a ground starch-containing material;
   (b) liquefying the ground starch-containing material with an alpha-amylase to produce a liquefied starch-containing material comprising a dextrin;
   (c) saccharifying the liquefied starch-containing material with a glucoamylase variant of claim 1 or a composition of claim 11 to produce a saccharified material comprising a sugar; and
   (d) fermenting the saccharified material with a fermenting organism.

14. A process of producing a fermentation product comprising:
   (a) grinding a starch-containing material that has not been wet milled to produce a ground starch-containing material;
   (b) saccharifying the ground starch-containing material with a glucoamylase variant of claim 1 or a composition of claim 11 at a temperature below the initial gelatinization temperature of the starch-containing material to produce a saccharified material comprising a sugar; and
   (c) fermenting the saccharified material with a fermenting organism.

15. A process of producing syrup comprising:
   (a) grinding a starch-containing material that has not been wet milled to produce a ground starch-containing material;
   (b) liquefying the ground starch-containing material with an alpha-amylase to produce a liquefied starch-containing material comprising a dextrin;
   (c) saccharifying the liquefied starch-containing material with a glucoamylase variant of claim 1 or a composition of claim 11 to produce a syrup.

16. The composition of claim 12, wherein the composition comprises:
   i) the variant of claim 1;
   ii) a *Rhizomucor pusillus* acid fungal alpha-amylase with *Aspergillus niger* glucoamylase linker and starch-binding domain (SBD); and
   iii) a *Thermoascus auranticus* protease.

* * * * *